(12) United States Patent
Morgan

(10) Patent No.: US 8,541,034 B2
(45) Date of Patent: *Sep. 24, 2013

(54) ELECTRICAL PRODUCING CREAMS

(76) Inventor: Clyde E. Morgan, Gardner, KS (US)

( * ) Notice: Subject to any disclaimer, the term of this patent is extended or adjusted under 35 U.S.C. 154(b) by 1389 days.

This patent is subject to a terminal disclaimer.

(21) Appl. No.: 11/866,573

(22) Filed: Oct. 3, 2007

(65) Prior Publication Data

US 2008/0069903 A1   Mar. 20, 2008

Related U.S. Application Data

(63) Continuation-in-part of application No. 11/220,138, filed on Sep. 6, 2005.

(60) Provisional application No. 60/608,136, filed on Sep. 8, 2004.

(51) Int. Cl.
| | |
|---|---|
| A61K 33/00 | (2006.01) |
| A61K 33/20 | (2006.01) |
| A61P 19/00 | (2006.01) |
| A61P 25/00 | (2006.01) |
| A61P 7/10 | (2006.01) |

(52) U.S. Cl.
USPC .......................................... 424/665; 424/722

(58) Field of Classification Search
USPC ....................................................... 424/446
See application file for complete search history.

(56) References Cited

U.S. PATENT DOCUMENTS

| | | | |
|---|---|---|---|
| 4,455,146 A | 6/1984 | Noda et al. | |
| 4,507,285 A * | 3/1985 | Kuhne | 424/615 |
| 4,623,346 A | 11/1986 | von Bittera et al. | |
| 4,627,852 A | 12/1986 | von Bittera et al. | |
| 4,661,104 A | 4/1987 | von Bittera et al. | |
| 4,702,916 A | 10/1987 | Geria | |
| 4,738,670 A | 4/1988 | von Bittera | |
| 4,795,638 A | 1/1989 | Ayache et al. | |
| 4,801,458 A | 1/1989 | Hidaka et al. | |
| 4,844,902 A | 7/1989 | Grohe | |
| 4,892,890 A | 1/1990 | Damani | |
| 4,963,591 A | 10/1990 | Fourman et al. | |
| 4,990,340 A | 2/1991 | Hidaka et al. | |
| 5,145,675 A | 9/1992 | Won | |
| 5,273,754 A | 12/1993 | Mann | |
| 5,352,437 A | 10/1994 | Nakagawa et al. | |
| 5,383,848 A | 1/1995 | Hillman et al. | |
| 5,429,590 A | 7/1995 | Saito et al. | |
| 5,468,492 A | 11/1995 | Szaloki et al. | |
| 5,505,958 A | 4/1996 | Bello et al. | |
| 5,597,849 A | 1/1997 | McGinity et al. | |
| 5,622,993 A | 4/1997 | McGinity et al. | |
| 5,626,856 A | 5/1997 | Berndt | |
| 5,665,386 A | 9/1997 | Benet et al. | |
| 5,716,621 A | 2/1998 | Bello et al. | |
| 5,716,625 A | 2/1998 | Hahn et al. | |
| 5,716,928 A | 2/1998 | Benet et al. | |
| 5,770,220 A | 6/1998 | Meconi et al. | |
| 5,780,047 A | 7/1998 | Kamiya et al. | |
| 5,804,173 A | 9/1998 | Hutchins et al. | |
| 5,804,203 A | 9/1998 | Hahn et al. | |
| 5,830,447 A | 11/1998 | Hutchins et al. | |
| 5,855,922 A | 1/1999 | Danner et al. | |
| 5,858,330 A | 1/1999 | Boltri et al. | |
| 5,863,527 A | 1/1999 | Hutchins et al. | |
| 5,866,143 A | 2/1999 | Elkhoury | |
| 5,882,663 A | 3/1999 | Koeniger et al. | |
| 5,891,463 A | 4/1999 | Bello et al. | |
| 5,916,548 A | 6/1999 | Hutchins et al. | |
| 5,916,566 A | 6/1999 | Benet et al. | |
| 5,942,233 A | 8/1999 | Chang | |
| 5,955,067 A | 9/1999 | Oge et al. | |
| 5,980,925 A | 11/1999 | Jampani et al. | |
| 6,103,266 A | 8/2000 | Tapolsky et al. | |
| 6,121,234 A | 9/2000 | Benet et al. | |
| 6,139,850 A | 10/2000 | Hahn et al. | |
| 6,139,876 A | 10/2000 | Kolta | |
| 6,143,317 A | 11/2000 | Himmelsbach et al. | |
| 6,174,891 B1 | 1/2001 | Nagase et al. | |
| 6,239,180 B1 | 5/2001 | Robbins | |
| 6,252,003 B1 | 6/2001 | Kuwahara et al. | |
| 6,258,857 B1 | 7/2001 | Iijima et al. | |
| 6,270,783 B1 | 8/2001 | Slavtchoff et al. | |

(Continued)

OTHER PUBLICATIONS

Ralph Moss, PhD.: The Moss Reports #64, Moss Reports on Spirulina (#64), 4 pages, www.annieappleseedproject.org/mosreponspir.html.
"What is Spirulina," 3 pages, www.naturalways.com/spirul1.htm.
"Aerobic 07 Stabilized Oxygen Water Purification Drops," 4 pages, http://www.baproducts.com/aerobic.htm.
Bicarbonates definition, 1 page (no other information available).
"Cellular Metabolism and Fermentation," 8 pages, http://www.emc.maricopa.edu/faculty/farabee/BIOBK/BioBookGlyc.html.
"Cellular Respiration," 5 pages, http://users.rcn.com/jkimball.ma.ultranet/BiologyPages/C/CellularRespiration.html.

(Continued)

*Primary Examiner* — Fereydoun G Sajjadi
*Assistant Examiner* — Audrea Buckley
(74) *Attorney, Agent, or Firm* — Hovey Williams LLP

(57) ABSTRACT

New electrical producing creams are provided. In one embodiment, the electrical producing creams comprise menthol and camphor, preferably provided as part of a base gel, supplemented with potassium and a source of oxygen. The most preferred base gel is sold under the name SOMBRA. In another embodiment, the electrical producing creams comprise potassium and a source of oxygen supplemented with optional active and inactive ingredients. The most preferred source of oxygen is a chlorite (e.g., sodium chlorite) and/or spirulina. The electrical producing creams provide high metabolic activities and sustain those activities over prolonged periods of time, thus being useful for treating a large variety of ailments, including diabetic neuropathy, post hepatic neuralgia, scleroderma, psoriasis, strain, spasticity, headaches, neuropathy secondary to drugs, peripheral neuropathy, leg pain, muscle cramps, muscle aches and pains, bruise, sinusitis, sprain, arthritis, joint pain (arthralgia), and edema.

11 Claims, 7 Drawing Sheets
(2 of 7 Drawing Sheet(s) Filed in Color)

(56) References Cited

U.S. PATENT DOCUMENTS

| | | | |
|---|---|---|---|
| 6,277,398 B1 | 8/2001 | Caruso | |
| 6,277,401 B1 | 8/2001 | Bello et al. | |
| 6,284,234 B1 | 9/2001 | Niemiec et al. | |
| 6,299,885 B1 | 10/2001 | Yamasaki et al. | |
| 6,306,412 B1 | 10/2001 | Crotty et al. | |
| 6,316,461 B1 | 11/2001 | Nagase et al. | |
| 6,328,982 B1 | 12/2001 | Shiroyama et al. | |
| 6,335,023 B1 | 1/2002 | Yu et al. | |
| 6,348,218 B1 | 2/2002 | Hed | |
| 6,359,032 B1 | 3/2002 | Kuwahara et al. | |
| 6,409,997 B1 | 6/2002 | Castro | |
| 6,419,913 B1 | 7/2002 | Niemiec et al. | |
| 6,432,415 B1 | 8/2002 | Osborne et al. | |
| 6,433,061 B1 | 8/2002 | Marchant et al. | |
| 6,440,987 B1 | 8/2002 | Nagase et al. | |
| 6,495,498 B2 | 12/2002 | Niemiec et al. | |
| 6,524,594 B1 | 2/2003 | Santora et al. | |
| 6,555,130 B2 | 4/2003 | Wustling et al. | |
| 6,559,168 B2 | 5/2003 | Marfat et al. | |
| 6,576,623 B1 | 6/2003 | Nakanishi et al. | |
| 6,579,543 B1 | 6/2003 | McClung | |
| 6,582,724 B2 | 6/2003 | Hsu et al. | |
| 6,586,000 B2 | 7/2003 | Luo et al. | |
| 6,592,896 B2 | 7/2003 | Rosenbloom | |
| 6,596,313 B2 | 7/2003 | Rosenbloom | |
| 6,623,756 B1 | 9/2003 | Wilber et al. | |
| 6,635,702 B1 | 10/2003 | Schmucker-Castner et al. | |
| 6,638,981 B2 | 10/2003 | Williams et al. | |
| 6,645,506 B1 | 11/2003 | Farmer | |
| 6,645,520 B2 | 11/2003 | Hsu et al. | |
| 6,646,012 B2 | 11/2003 | Choi et al. | |
| 6,649,633 B2 | 11/2003 | Chambers et al. | |
| 6,653,352 B2 | 11/2003 | Barr et al. | |
| 2002/0114849 A1 | 8/2002 | Camper et al. | |
| 2006/0051432 A1 | 3/2006 | Morgan | |

OTHER PUBLICATIONS

TerBeek, Kenneth J., "Explosion with Sodium Chlorite," Chemical & Engineering News, Mar. 22, 1993, vol. 71, No. 12, p. 4.

Youn, Brian A., MD., "Oxygen and its Role in Wound Healing," Geisinger Medical Center, 5 pages.

Ali, Majid MD., "Seven Aspects of Oxygen & Oxidation," 3 pages, http://majidali.com/seven.htm.

Two paragraph description of Spirulina, 1 page, http://www.spirulinasource.com/earthfoodch!a.html.

Six paragraph description of Spirulina Pacifica, 1 page (no other information available).

"Spirulina: Huge Health Benefits," 8 pages, http://www.relfe.com/spirulina_heath_benefits.html, www.relfe.com//spirulina_health_benefits%20_2.html, www.relfe.com//spirulina_health_benefits%20_3.html.

Hofbauer, Gess B. et al., "The Cellular Oxygen Tension Regulates Expression of the Endoplasmic Oxidoreductase ER01-Lalpha," Eur. J. Biochem., 270, 2228-2235 (2003), Instit fur Physiologie der Universitat Regensburg, Germany, http://content.febsjournal.org/cgi/content/full/270/10/2228.

Stabilized Oxygen Supplement from WaterOz, 3 pages, http://wateroz.jeffotto.com/products/oxygen.htm.

ATP—The Universal Energy Carrier in the Living Cell, Boyer et al., 10 pages, http://www.eyesight.org/Research/Research-ATP/research-atp.html.

Deficiencies Caused by IBD, 3 pages (no other information available).

Neuropathy, ReBuilder Materials, 9 pages (no other information available).

Klabunde, Richard E. PhD., "Metabolic Mechanisms of Vasodilation," Revised Aug. 29, 2005, 3 pages, http://www.cvphysiology.com/Blood%20Flow/BF008.htm.

Abbott, G.W. et al., "MiRP2 Forms Potassium Channels in Skeletal Muscle with Kv3.4 and is Associated with Periodic Paralysis," Cell, 104:217-231, Jan. 26, 2001 http://www.ncbi.nlm.nih.gov/entrez/query.fcgi?cmd=Retrieve&db=PubMed&Lis_uids=112 . . . .

Misner, Bill, PhD., "Muscle Cramps: Dealing with Heat Stress During Endurance Exercise," 6 pages, http://www.fit-zone.com/library/E/Endurance_Training/cramps.html.

Muscle Spasms 3 pages (no other information available).

Muscles, Aug. 26, 2004, 12 pages, http://users.erols.com/jkimball.ma.ultranet/BiologyPages/M/Muscles.html.

Na+/K+ (Sodium/Potassium) Pump, 1 page (no other information available).

Nerve Impulses, Updated Apr. 17, 2004, 14 pages, http://www.biologymad.com/NervousSystem/nerveimpulses.htm.

Neuropathy and Diabetes, ReBuilder Materials, 4 pages (no other information available).

Potassium, 18 pages, http://www.ithyroid.com/potassium.htm.

Haas, Elson M. MD., "Potassium," 5 pages, http:www.healthy.net/scr/article.asp?ID=2063.

Dr. T. Dixon, Potassium Balance, 12 pages, http://www.uhmc.sunysb.edu/internalmed/nephro/webpages/Part_D.htm.

"Potassium is a Mineral that is Required in Significant Amounts for Human Health. Potassium Balances Sodium in the Body to Regulate Hydration." Diagnose-Me: Condition: Potassium Need, 2 pages, http://www.diagnose-me.com/cond/C424831.html.

Potassium, 2 pages, http:www.elementalresearchllc.com/potassium.htm.

"Potassium is required for . . . ," 13 brief paragraphs regarding potassium, 2 pages (no other information available).

Weber, Charles MS., "Potassium Nutritional Losses and Recommended Daily Requirement," Updated Jan. 2005, 13 pages, http://members.tripod.com/~charles_W/arthritis8.html.

Potassium with Magnesium Citrate, 3 pages, http://wwwo.organicfood.co.uk/vns/potassium-magcit.html.

Potassium, The Linus Pauling Institute, 9 pages, http://lpi.oregonstate.edu/inforcenter/minerals/potassium/.

Pyruvate Kinase, 10 pages, http:www.worthington-biochem.com/PKL/default.html.

Transport In and Out of Cells, 12 pages, http://www.emc.maricopa.edu/faculty/farabee/BIOBK/BioBooktransp.html.

Joint Inflammation, 5 pages (no other information available).

Contusion; Hematoma, 2 pages (no other information available).

Cramps—muscle, 2 pages (no other information available).

Nerve damage—diabetic, 2 pages (no other information available).

Edema; Anasarca, 3 pages (no other information available).

Stiffness in a joint; Pain—joints; Arthralgia, 3 pages (no other information available).

Pain—leg; Aches—leg; Cramps—leg, 3 pages (no other information available).

Muscle pain; Myalgia; Pain—muscles, 3 pages (no other information available).

Peripheral neuritis; Neuropathy—peripheral; Neuritis—peripheral, 5 pages (no other information available).

Neuropathy secondary to drugs . . . , 2 pages (no other information available).

Nerve pain; postherpetic neuralgia, 4 pages (no other information available).

Plaque psoriasis, 3 pages (no other information available).

Acute sinusitis; Sinus infection; Sinusitis—acute, 4 pages (no other information available).

Spasticity is a condition described by stiff or rigid muscles . . . , 2 pages (no other information available).

Joint Sprain, 2 pages (no other information available).

Pulled Muscle, 1 page (no other information available).

Muscle contraction headache; Benign headache; Headache—tension, 3 pages (no other information available).

"Below is a list of symptoms and diseases that have positive results . . . ," Definitions taken from Medline Plus Medical Encyclopedia, 1 page (no other information available).

Atkins, David. L., "A Tutorial in Basic Neurobiology," 61 pages, http://sky.bsd.uchicago.edu/lcy_ref/synap/resting.html.

Sombra, Natural Pain Relieving Gel, 1 page, http:www.sombrausa.com/somingpg.htm.

Earthrise Spirulina Dietary Supplement Capsules (Photograph of Bottle), 4 pages.

Nature's Way Potassium Chelate Capsules (Photograph of Bottle), 3 pages.

CC Medical Devices, Inc. My Alivio Cream (Photograph of Bottle), 2 pages.
http://www.patentstorm.us/patents/6337327-description.html, Patent Storm, "Pharmaceutical Compositions Comprising an Aldose Reductase Inhibitor and an Ace Inhibitor," U.S. Patent No. 6,337,327, Cameron et al., Jan. 8, 2002.
Office Action dated May 28, 2008 in corresponding U.S. Appl. No. 11/220,138.
Office Action dated Dec. 24, 2008 in corresponding U.S. Appl. No. 11/220,138.
Office Action dated Jun. 24, 2009 in corresponding U.S. Appl. No. 11/220,138.
Written Opinion and Search Report dated Jan. 24, 2007 in corresponding application PCT/US05/31819 filed on Sep. 7, 2005.
International Report on Patentability dated Apr. 3, 2007 in corresponding application PCT/US05/31819 filed on Sep. 7, 2005.
Lubrizol, Personal Care Noveon Consumer Specialties, Products Carbopol Rheology Modifiers, www.personalcare.noveon.com/products/carbopol/ultrez20.asp, 2007, 2 pages.
Sore No More, Natremed, Thursday, Aug. 9, 2007, www.sorenomoreuk.com, 2 pages.
Lotioncrafter, Suttocide® A: INCI: Sodium Hydroxymethylglycinate, 2 pages.
"The cells of excitable tissues . . . ," Sherwood, Stryer, 2001 and 1995, 2 pages.
Lee et al., "Structure of the KvAP voltage-dependent K+ channel and its dependence on the lipid membrane," Proc Natl Acad Sci U.S.A., Oct. 25, 2005;102(43):15441-6, 1 page.

* cited by examiner

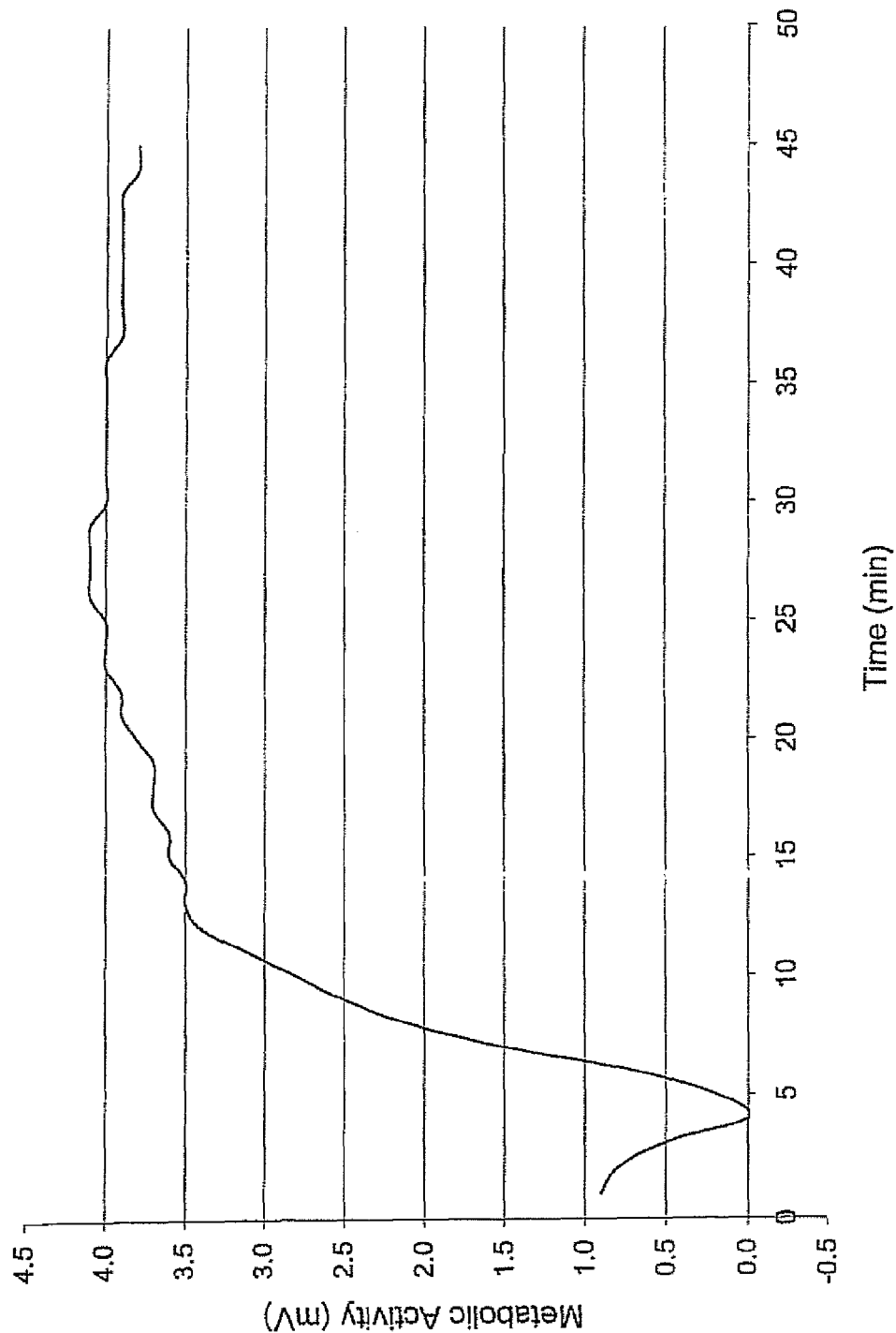

ELECTRICAL PRODUCING CREAMS

RELATED APPLICATIONS

This application is a continuation-in-part of U.S. patent application Ser. No. 11/220,138, filed on Sep. 6, 2005, which claims the priority benefit of U.S. Provisional Patent Application No. 60/608,136, filed Sep. 8, 2004, each of which is incorporated by reference herein.

BACKGROUND OF THE INVENTION

1. Field of the Invention

The present invention is broadly concerned with improved electrical producing creams in forms of creams, lotions, gels or solids which are useful in the treatment of a variety of conditions that are ameliorated by increased cell metabolism, circulation, and nerve function. More particularly, in one embodiment, the invention is concerned with electrical producing creams having a gel base with menthol and camphor, and supplemented with potassium and an oxygen source such as an alkali metal chlorite. In another embodiment, the invention is concerned with electrical producing creams having potassium and an oxygen source such as an alkali metal chlorite, and optionally including one or more active ingredients such as menthol and/or camphor and/or capsicum.

2. Description of the Prior Art

A variety of topically applied creams and lotions have been developed in the past for treatment of conditions such as arthritis and muscle pains. One such product is commercialized under the designation SOMBRA. This product contains 3% menthol and 3% camphor, in a gel base, and is used for the temporary relief of minor aches and pains of muscles and joints associated with simple backaches, arthritis, strains, bruises, and sprains. Another such product is commercialized under the name BioFreeze. This product is also used for the temporary relief of pain, and contains 3.5% menthol and 0.2% camphor, in a gel base. Another such product is commercialized under the designation Icy Hot Extra Strength. This product contains 30% methyl salicylate and 10% menthol.

However, many prior art creams and lotions do not adequately treat these conditions in most people. Furthermore, even those that are successful do not sustain metabolic activity for extended periods of time, thus making any relief experienced rather temporary. There is a need for new treatments that provide relief for a wide variety of conditions and for extended periods of time.

SUMMARY OF THE INVENTION

The present invention overcomes these problems by broadly providing novel electrical producing creams having improved metabolic activity through small electrical charges (in mV) in contact with dendrite channels.

In more detail, the inventive electrical producing creams comprise menthol, camphor, potassium, and a source of oxygen. The menthol and camphor can be individually added to the composition, or they can be added via a base composition including menthol, camphor, and capsicum. One preferred base composition is a gel sold under the name SOMBRA. Regardless of the delivery source, the menthol is preferably present in the electrical producing cream at a level of at least about 0.5% by weight, more preferably from about 2-20% by weight, and even more preferably from about 2-4% by weight, based upon the total weight of the electrical producing cream taken as 100% by weight. Furthermore, the camphor is preferably present in the electrical producing cream at a level of at least about 0.5% by weight, more preferably from about 2-20% by weight, and even more preferably from about 2-4% by weight, based upon the total weight of the electrical producing cream taken as 100% by weight.

The potassium is preferably provided in powder form, and it can be obtained from dietary supplements, for example. One preferred source of potassium is potassium chlorite. More preferably, the potassium chlorite is Potassium Chelate (99 mg potency) sold by Nature's Way. Potassium Chelate is provided in the form of a capsule including powder potassium and minor amounts of ground millet. The capsule can simply be opened, and the powder from the capsule used in the present invention. Potassium is preferably present in the electrical producing cream at a level of at least about 0.02% by weight, more preferably from about 0.04-0.5% by weight, and even more preferably from about 0.09-0.2% by weight, based upon the total weight of the electrical producing cream taken as 100% by weight. When Potassium Chelate or a similar product is used, preferably from about 1-20 capsules, more preferably from about 1-15 capsules, and even more preferably from about 8-13 capsules are used.

The source of oxygen can be any source that is capable of delivering the appropriate levels of oxygen to the electrical producing cream. Suitable oxygen sources include those selected from the group consisting of chlorites (and preferably alkali metal chlorites such sodium chlorite and magnesium chlorite), spirulina, and mixtures of the foregoing. The most preferred oxygen source is sold under the name AEROBIC 07, which contains deionized water, sodium chlorite, carbonates, and bicarbonates.

The oxygen source is preferably present in the electrical producing cream in sufficient quantities to provide oxygen levels of at least about 0.016% by weight, more preferably from about 0.10-0.85% by weight, and even more preferably from about 0.17-0.25% by weight, based upon the total weight of the electrical producing cream taken as 100% by weight. When AEROBIC 07 or a similar product is used, it is preferably added at levels of from about 1-13 drops, more preferably from about 1-10 drops, and even more preferably about 4 drops.

In one alternative embodiment, the electrical producing cream also includes a source of chlorine ions. If sodium chlorite is used as the source of oxygen, it will also functions as a source of chlorine ions. Other suitable sources of chlorine ions include any chlorite (e.g., sodium hypochlorite) such as those found in commercially available bleaching agents (e.g., CLOROX, CALIBEX). In these embodiments, the source of chlorine is included in sufficient quantities to provide chlorine ion levels of from about 0.10-10% by weight, and more preferably from about 0.16-0.85% by weight, based upon the total weight of the electrical producing cream taken as 100% by weight.

The inventive electrical producing creams can also include a number of optional ingredients, depending upon the final use. Some suitable ingredients include those selected from the group consisting of aloe vera extract, carbomer, decyl plyglucose, deionized water, grapefruit seed extract, green tea extract, orange peel extract, queen of the prairie extract, rose water, silica, sodium hydroxymethyl glycinate, vegetable glycerin, witch hazel, yucca extract, carbonates, bicarbonates, and mixtures of the foregoing. The preferred quantities of these ingredients are set forth in Table 1. These ingredients can be added individually or in a group as part of another composition (e.g., in a base composition such as SOMBRA).

TABLE 1

| INGREDIENT | BROAD RANGE[A] | MORE PREFERRED RANGE[A] |
|---|---|---|
| *Aloe Vera* Extract | 0.10-50% | 0.25-1.75% |
| Capsaicin | 0.001-10% | 0.25%-1.75% |
| Carbomer | 1.35-30% | 2.75-19.25% |
| Decyl Plyglucose | 0.1-9% | 0.5-3.5% |
| Deionized Water | 20-90% | 76.5-90% |
| Grapefruit Seed Extract | 0.001-5% | 0.25-1.75% |
| Green Tea Extract | 0.05-10% | 0.5-3.5% |
| Orange Peel Extract | 0.001-5% | 0.25-1.75% |
| Queen of the Prairie Extract | 0.25-20% | 2.25-15.75% |
| Rose Water | 0.2-7% | 0.5-3.5% |
| Silica | 0.03-20% | 1-7% |
| Sodium Hydroxymethyl Glycinate | 0.05-25% | 1.25-8.75% |
| Vegetable Glycerin | 0.09-50% | 1.75-12.25% |
| Witch Hazel | 0.02-15% | 1-7% |
| *Yucca* Extract | 0.015-30% | 0.5-3.5% |
| Carbonates | 0.025-3.5% | 0.25-1.75% |
| Bicarbonates | 0.025-3.5% | 0.25-1.75% |

[A]The percentages by weight are based upon the total weight of the topical electrical producing cream taken as 100% by weight.

The inventive electrical producing creams are formed by simply mixing the above ingredients together, preferably in some type of carrier. If SOMBRA is used, then the carrier is provided by that product.

In a particularly preferred preparation method, a precursor composition containing the camphor and menthol is provided. The precursor composition should comprise:

from about 1-10% by weight menthol, preferably from about 1-5% menthol, and even more preferably about 3% by weight menthol; and from about 1-10% by weight camphor, preferably from about 1-5% camphor, and even more preferably about 3% by weight camphor, based upon the total weight of the electrical producing cream taken as 100% by weight.

The precursor composition can also include some or all of the optional ingredients discussed above.

A quantity of the precursor composition is added to a container, along with a portion of the potassium. Further respective quantities of the precursor composition and potassium are then added in alternating steps until the desired quantity as been obtained. The precursor composition and potassium within the container are preferably then mixed until substantially homogeneous (e.g., from about 1-3 minutes, and preferably about 2 minutes). Mixing can be carried out by hand or mechanical mixing means (e.g., mixer, shearing in industrial equipment). The source of oxygen is then added to the resulting mixture and further mixing is carried out. Any optional ingredients that were not already added can then be added to the mixture to yield the final electrical producing cream.

In another embodiment, the inventive electrical producing creams comprise potassium and a source of oxygen. Potassium is preferably present in the electrical producing cream at a level of from about 0.005% to about 15% by weight, more preferably from about 0.16% to about 7.0% by weight, and even more preferably from about 0.06% to about 0.12% by weight, based upon the total weight of the electrical producing cream taken as 100% by weight. The source of oxygen can be any source that is capable of delivering the appropriate levels of oxygen to the electrical producing cream. In a particularly preferred embodiment the oxygen source is an alkali metal chlorite, such as sodium chlorite. The oxygen source is preferably present in the electrical producing cream in sufficient quantities to provide oxygen levels of from about 0.005% to about 15% by weight, more preferably from about 0.016% to about 7.0% by weight, and even more preferably from about 0.01% to about 0.05% by weight, based upon the total weight of the electrical producing cream taken as 100% by weight.

The electrical producing cream may also optionally include one or more active ingredients selected from the group consisting of analgesics, anesthetics, antipruritics, antihistamines, and counterirritants. More preferably the active ingredients are selected from the group consisting of menthol, camphor, and capsicum. If present, the active ingredient may be individually added to the composition, or the menthol and/or camphor and/or capsicum can be added via a commercially-available base composition including menthol and/or camphor and/or capsicum. Regardless of the delivery source, the camphor, when included, is preferably present in the electrical producing cream at a level of from about 0.005% to about 22.0% by weight, more preferably from about 0.030% to about 11.0% by weight, and even more preferably from about 2.90% to about 3.30% by weight, based upon the total weight of the electrical producing cream taken as 100% by weight. The menthol, when included, is preferably present in the electrical producing cream at a level of from about 0.005% to about 20% by weight, more preferably from about 1.250% to about 16.0% by weight, and even more preferably from about 2.80% to about 3.20% by weight, based upon the total weight of the electrical producing cream taken as 100% by weight. The capsicum, when included, is preferably present in the electrical producing cream at a level of from about 0.001% to about 8% by weight, more preferably from about 0.025% to about 0.250% by weight, and even more preferably from about 0.220% to about 0.300% by weight, based upon the total weight of the electrical producing cream taken as 100% by weight.

As will be appreciated by those in the art, although menthol and/or camphor and/or capsicum are particularly preferred active ingredients, other active ingredients known in the art can be substituted in the electrical producing electrical producing cream. Examples of suitable active ingredients (analgesics, anesthetics, antipruritics, antihistamines, and counterirritants) approved by the FDA and which can be included in the inventive electrical producing cream in amounts in accordance with FDA monographs include, but are not limited to: bensocaine, butamben picrate, dibucaine, dibucaine hydrochloride, dimethisoquin hydrochloride, dyclonine hydrochloride, lidocaine, lidocaine hydrochloride, pramoxine hydrochloride, tetracaine, tetracaine hydrochloride, benzyl alcohol, camphor with phenol, camphorated metacresol, juniper tar, phenol, phenol with camphor, phenolate sodium, resoronol, diphenlydramine hydrochloride, tripelennamine hydrochloride, hydrocortisone, hydrocortisone acetate, allyl isothiocyante, ammonia, methyl salicyate, turpentine oil, histamine dihydrochloride, methyl nicotinate, and capsicum oleoresin. The preferred quantities of additional active ingredients that are particularly preferred substitutes in the inventive electrical producing creams are set forth in Table 2 below.

TABLE 2

| ACTIVE INGREDIENT | BROAD RANGE[A] | MORE PREFERRED RANGE[A] | MOST PREFERRED RANGE[A] |
|---|---|---|---|
| Allyl Isothiocyanate | 0-10% | 0.480-5.0% | 0.50-0.520% |
| Ammonia | 0-5.0% | 0.98-2.5% | 1.0-1.20% |
| Methyl Salicyate | 0-95% | 9.8-60.0% | 10-10.20% |
| Turpentine Oil | 0-95% | 5.80-50.0% | 6.0-6.20% |

TABLE 2-continued

| ACTIVE INGREDIENT | BROAD RANGE[A] | MORE PREFERRED RANGE[A] | MOST PREFERRED RANGE[A] |
|---|---|---|---|
| Histamine Dihydrochloride | 0-0.20% | 0.020-0.10% | 0.025-0.030% |
| Methyl Nicotinate | 0-2% | 0.240-1.0% | 0.250-0.260% |
| Capsicum Oleoresin | 0-0.5% | 0.025-0.300% | 0.220-0.250% |

The inventive electrical producing creams can also include a number of optional ingredients depending upon the final use. Some suitable ingredients include those selected from the group consisting of aloe vera, arnica, bosweila, bromelaine, carbonates and bicarbonates, decyl gluco side, distilled water, deionized water, ginger, glycerine, green tea extract, sodium hydroxymethylglycinate, willow bark, witch hazel, fragrance, thickener, and mixtures of the foregoing. The preferred quantities of these ingredients are set forth in Table 3. These ingredients can be added individually or in a group as part of another composition. In a particularly preferred embodiment, the thickener comprises a carbomer polymer, such as a high molecular weight homo- or copolymer of acrylic acid crosslinked with a polyalkenyl polyether. Preferred thickeners are commercially available under the name Carbopol®, and are available in powder or liquid form. A particularly preferred thickener is Carbopol® Ultrez 20. Other thickeners that may be used in the inventive electrical producing creams include: cetearyl alcohol, cetyl alcohol, and sodium alginate.

TABLE 3

| INGREDIENT | BROAD RANGE[A] | MORE PREFERRED RANGE[A] | MOST PREFERRED RANGE[A] |
|---|---|---|---|
| Aloe Vera | 0.02-89% | 0.06-44.95% | 0.1-0.9% |
| Arnica | 0-20% | 0.05-10.3% | 0.1-0.6% |
| Bosweila | 0-10% | 0.003-5.01% | 0.005-0.02% |
| Bromelaine | 0-10% | 0.003-5.01% | 0.005-0.02% |
| Carbonates | 0.002-10% | 0.004-5.01% | 0.005-0.02% |
| Bicarbonates | 0.002-10% | 0.008-5.01% | 0.005-0.02% |
| Decyl Glucoside | 0.01-10% | 0.405-5.55% | 0.8-1.1% |
| Distilled/Deionized Water | 0-93% | 35-91.5% | 70-90% |
| Ginger | 0-10% | 0.003-5.01% | 0.005-0.02% |
| Glycerine | 0-20% | 1.5-13% | 3-6% |
| Green Tea extract | 0-10% | 0.003-5.15% | 0.005-0.3% |
| Sodium Hydroxymethyl Glycinate | 0.10-3% | 0.45-2% | 0.80-1% |
| Willow Bark | 0-10% | 0.003-5.15% | 0.005-0.3% |
| Witch Hazel | 0-15% | 1-9.5% | 2-4% |
| Thickener | 0-10% | 0.2-5.5% | 0.4-1% |
| Fragrance | 0-20% | 0.05-10.2% | 0.1-0.4% |

[A]The percentages by weight are based upon the total weight of the topical electrical producing cream taken as 100% by weight.

The inventive electrical producing creams are formed simply by mixing or shaking the above ingredients together (with or without the optional ingredients), preferably in some type of container or carrier.

The amount of thickener present in the electrical producing cream can be varied and will depend upon the final desired viscosity and consistency of the inventive electrical producing creams. The inventive electrical producing cream can be provided in a variety of final forms selected from the group consisting of cream, lotion, gel, solid stick, and sprayable aqueous formulations.

The inventive topical electrical producing cream is used to treat a portion of the body (human or animal) afflicted with an ailment by simply contacting the electrical producing cream with the afflicted portion of the body. The electrical producing cream is then preferably rubbed into the skin until it is no longer visible. While the cream is neither an antiseptic nor an antimicrobial, it will be appreciated that the electrical producing cream can be used to treat and/or relieve numerous conditions, including diabetic neuropathy, post hepatic neuralgia, scleroderma, psoriasis, restless legs syndrome, muscle spasms, tremors associated with Parkinson's and other neurological disorders, strain, spasticity, headaches, neuropathy secondary to drugs, peripheral neuropathy, leg pain, muscle cramps, muscle aches and pains, bruise, sinusitis, sprain, arthritis, joint pain (arthralgia), and edema. In particular, the inventive electrical producing creams are useful for reducing swelling and providing relief from all forms of arthritis, acute joint and/or muscle pain, chronic joint and/or muscle pain, neck and back pain, shoulder muscle and joint area pain, muscle spasms, strained muscles, sports injuries, menstrual pain, swollen discomfort breast, pelvic pain. The inventive electrical producing creams can also be used for therapeutic or relaxation massage, as well as a skin firming cream. In one embodiment the electrical producing cream is provided for therapeutic massage and comprises potassium and sodium chlorite, in addition to active ingredients selected from the group consisting of menthol, camphor, and capsicum in amounts that are below the FDA monograph. In another embodiment, the electrical producing cream is provided for relaxation massage and comprises potassium and sodium chlorite. The term antiseptic, as used herein, is intended to mean a substance that inhibits the growth and development of microorganisms. The term antimicrobial, as used herein, is intended to mean a drug or other composition used to fight infections caused by bacteria, fungi, and viruses.

In addition to alleviating pain, the inventive electrical producing cream offers a particularly significant advantage in that it achieves high metabolic activity and maintains that activity over extended periods of time. "Metabolic activity" as used herein refers to energy (in mV) that is created by the potassium ions in the electrical producing cream. That energy is then transferred to the patient at the electrical producing cream location on the skin. An ion channel is an integral cell membrane protein and controls the small voltage gradient across the plasma membrane of all living cells by allowing the flow of ions down their electrochemical gradient. Voltage-gated channels such as sodium or potassium channels, open and close in response to membrane potential. These channels are common in all cells, but are critical in excitable tissues such as neurons and muscle tissue. Though not wishing to be bound by theory, it is believed that the energy created by the electrical producing cream excites and thus opens the sodium-potassium pumps in the cells. This stimulates the nervous system and better allows active ingredients to enter the cells, over an extended period of time. In particular, based upon results from voltage meter testing, thermal imaging, muscle testing, reflex testing, two point discrimination testing, and nerve conduction testing, the electrical producing cream has been found to activate and reactivate itself through interaction with the body's own metabolic tissues and waste.

Metabolic activity is determined by mixing 1 g of a electrical producing cream with 0.1 g of a commercially available electrolyte material (e.g., one sold under the name ORAL REHYDRATION SALTS, available from Jianas Bros. Packaging Co.). The mixture is then placed onto an electrogel pad, which is "sandwiched" between two ECG patches connected to a voltmeter. Readings in mV are taken over regular intervals (e.g., 5-minute intervals).

When using the electrical producing creams of the invention, a peak (i.e., highest or maximum) metabolic activity of at least about 10 mV, preferably at least about 30 mV, more preferably at least about 40 mV, and even more preferably from about 40 to about 70 mV is achieved. This peak is preferably achieved within about 30 minutes, and more preferably within about 15 minutes, of application to the afflicted area.

The inventive electrical producing creams also possess the property of having a retained metabolic activity of at least about 20%, preferably at least about 30%, and even more preferably from about 50-100% over a 45-minute time period. Furthermore, the inventive electrical producing creams possess the property of having a retained metabolic activity of at least about 5%, preferably at least about 20%, and even more preferably from about 25-100% over an 8-hour time period. As used herein, "retained metabolic activity" is determined as follows:

$$\text{Retained Metabolic Activity} = \left[ \frac{\text{metabolic activity after 45 minutes or 8 hours}}{\text{peak metabolic activity}} \right] \times 100$$

The inventive electrical producing cream has also been found to improve cell metabolism, circulation, and nerve function, alleviating symptoms from nerve pain associated with shingles, and peripheral neuropathy caused by diabetes, radiation treatment, chemotherapy, or unknown causes. For example, in the case of shingles, the electrical producing cream does not attack the virus itself, but rather increases nerve function to alleviate the symptoms caused by the virus. In addition, the inventive electrical producing cream can also be used to stimulate and increase nerve function where the nerves have been damaged by a disease such as multiple sclerosis or spinal chord injuries, by providing a feedback mechanism by stimulating neurons and dendrites through the small electrical force (mV). Specifically, the metabolic activity of the inventive electrical producing cream creates a small electrical force (mV) that stimulates the dendrites at the ends of neurons.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1c is a graph depicting the metabolic activity of the inventive electrical producing cream over a 45-minute time period;

DETAILED DESCRIPTION OF THE PREFERRED EMBODIMENTS

Examples

Figure 1A:
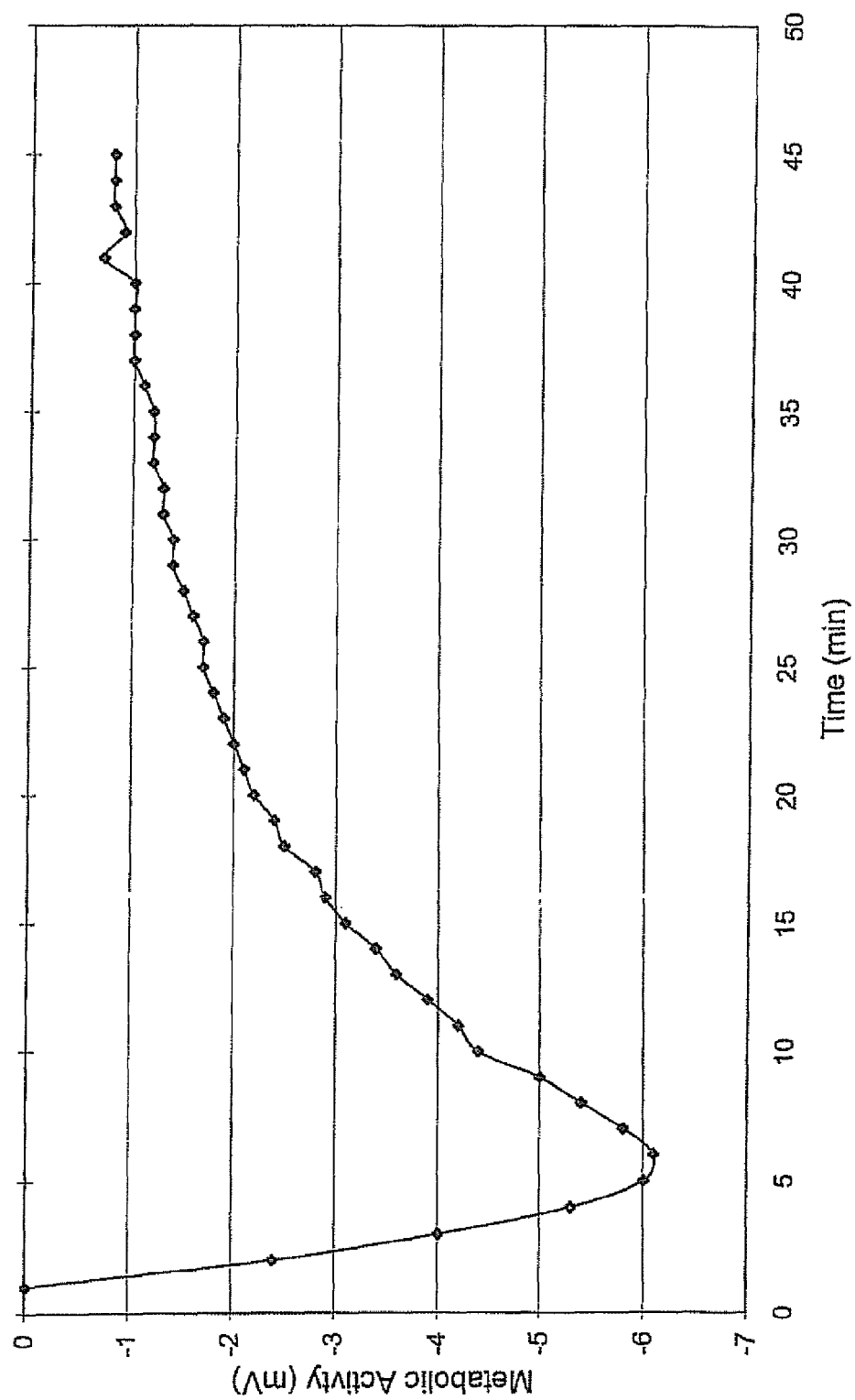
FIG. 1a is a graph depicting the metabolic activity of a prior art product over a 45-minute time period.

The following examples set forth preferred methods in accordance with the invention. It is to be understood, however, that these examples are provided by way of illustration and nothing therein should be taken as a limitation upon the overall scope of the invention.

Example 1

Preparation of Topical Electrical Producing Cream

A 1-gallon plastic jug was tared on a Sunbeam Model SP5 top balance (no shield, small pan balance). The jug was then charged with 5.7 oz of SOMBRA Natural Pain Relieving Gel (available from Sombra Inc., Albuquerque, N. Mex.).

Thirteen potassium amino acid chelate capsules (99 mg potassium with millet filler; available from Nature's Way, Springville, Utah) were emptied three at a time. The filled capsule weight was 0.78 g, the emptied powder weight was 0.67 g, and the empty capsule weight was 0.67 g (n=1). The level of elemental potassium in the capsule was not given on the label.

The powder emptied from the capsules was then added to the SOMBRA in the plastic jug as follows:

(1) The jug was charged with SOMBRA to a weight of 12.1 oz., and the powder from three empty capsules was added;

(2) The jug was charged with SOMBRA to a weight of 1 lb. 6.1 oz., and the powder from three empty capsules was added;

(3) The jug was charged with SOMBRA to a weight of 2 lb. 3.9 oz., and the powder from the remaining empty capsules was added; and (4) The jug was charged to a final weight of 3 lb. 1 oz. with SOMBRA.

A cap was placed on the jug, and the jug was shaken by hand for about 2 minutes to substantially evenly distribute the powder. The gel did not adhere to the plastic jug after the potassium amino acid chelate was added.

AEROBIC 07 (a dietary supplement including deionized water, sodium chlorite, carbonates, and bicarbonates; available from Aerobic Live, Phoenix, Ariz.) was used as a stabilized source of oxygen. Thirteen drops of the Aerobic 07 were added to the plastic jug containing the SOMBRA-potassium amino acid chelate mixture. The jug was again capped and shaken by hand for about 2 minutes to yield the final electrical producing cream. The final electrical producing cream was more viscous than the SOMBRA gel. When comparing a quantity of each, the compounded electrical producing cream did not separate or flow as compared to the SOMBRA gel, which showed some physical separation.

Example 2

Treatment of Patient A

1. Patient History

The topical electrical producing cream prepared in Example 1 was used to treat a patient (hereinafter referred to as "Patient A"). Patient A was a Caucasian female in her 60s, and she was 5'7" and approximately 220 lb. Patient A exhibited neuropathy of the legs and feet, with the left leg being worse than the right. Patient A's big toe on her right foot and second toe on her left foot were amputated within the preceding 3 years due to diabetes. She had received angioplasty about 9 months prior, and the angioplasty improved blood flow to her lower extremities.

Both legs below the knees presented open sores about half-way between the knee caps and ankles. The sores were worse on the right leg than the left. She had used Bactroban and Betadine to treat the topical sores for infection.

Patient A also had an ulcer on the bottom of her right foot. She had begun a second, 2-3 week treatment course of Regranex, applying at bedtime. Previous use of Regranex had worked, but the ulcer recurred, so she then had surgery. She began to use Etherex, which she stated is a generic medicine for Regranex and Bactroban. Her daily medications are shown in Table A-B.

TABLE A

| PRESCRIPTION MEDICATION | DOSAGE |
|---|---|
| Lisinopril 20/12.5 | 2 p.o. qd |
| Atenolol 50 mg | 1½ p.o. qd |
| Lipitor 40 mg | 1 p.o. qd |
| Insulin | 40 u of N and 10 u of Humalog in morning; 40 u of N and 10 u of Humalog before dinner |
| Paroxitine (Paxil) 40 mg | p.o. qd |
| Levothyroxine 0.3 mg | p.o. qd |
| Calcitrol 0.25 μg | 1 p.o. bid |
| Niaspan 500 mg | 1 p.o. q evening |
| Plavix 75 mg | 1 p.o. qd |
| Furosemide 80 mg | p.o. 1 daily |
| Diovan 320 mg | 1 daily |
| Procrit | 1 injection q 2 weeks until no longer needed |
| Dynacirc 5 mg | 1 p.o. daily |

TABLE B

| VITAMINS AND OVER-THE-COUNTER MEDICATIONS | DOSAGE |
|---|---|
| Multivitamin | 1 p.o. daily |
| Prilosec | 1 p.o. daily |
| Low-Dose Aspirin | 1 every evening |
| Iron | 2 "pills" each day for anemia |

Patient A also reported using Walitin (generic for Claritin) and Nasonex as needed for allergies.

2. Treatment with Inventive Electrical Producing Cream

The ambient temperature during treatment ranged from 74-78° F. according to measurements from four different Stress Thermometers used "as is" (Dr. Lowenstein's Model SC911 accuracy +/−1.8° F., 10 ft. lead with fast temperature sensor).

Patient A was recumbent on a treatment table with a triangular pillow positioned behind both knees so that the knees were bent upward to rise above the ankles. A temperature probe was strapped on each upper ventral thigh and on the inside of each ankle. The probes were covered, and no electrical producing cream was applied to the probes. Equilibration time was approximately 10 minutes after the patient reclined in the prone position. After equilibration time was reached, the temperatures were recorded as shown in Table C.

TABLE C

| PROBE LOCATION | TEMPERATURE |
|---|---|
| right thigh | 90.0° F. |
| left ankle | 86.7° F. |
| right thigh | 92.3° F. |
| right ankle | 90.1° F. |

The inventive electrical producing cream was applied to the top and bottom of each thigh and later (as shown in Table D) to the top and bottom of each calf, ankle, and foot. The product was massaged into the skin until nearly invisible to the eye. The dosage level was 0.3 oz. on each thigh and each ankle for a total per leg dosage of 0.6 oz.

Temperature readings were taken at intervals, beginning 5 minutes after application to Patient A's legs. These readings are set forth in Table D.

TABLE D

| TIME | LOCATION | TEMPERATURE (° F.) |
|---|---|---|
| 5 minutes[A] | left thigh | 90.5 |
| | left ankle | 86.9 |
| | right thigh | 92.3 |
| | right ankle | 90.9 |
| Note - Patient A reported feeling heat at 5 minutes. | | |
| 7 minutes | left thigh | 90.9 |
| | left ankle | 86.9 |
| | right thigh | 92.3 |
| | right ankle | 90.9 |
| 10 minutes | left thigh | 91.5 |
| | left ankle | 86.9 |
| | right thigh | 92.5 |
| | right ankle | 91.2 |
| Note - Patient A reported heat at same level as at 5 minutes. | | |
| 15 minutes | left thigh | 91.4 |
| | left ankle | 87.1 |
| | right thigh | 92.1 |
| | right ankle | 90.7 |
| Note - Patient A reported feeling a warm sensation. There was sweat behind the left knee. Electrical producing cream was applied to left ankle at 17 minutes. A paper towel was placed on the triangular pillow. | | |
| 20 minutes | left thigh | 91.2 |
| | left ankle | 86.7 |
| | right thigh | 91.9 |
| | right ankle | 90.1 |
| 25 minutes | left thigh | 91.2 |
| | left ankle | 86.5 |
| | right thigh | 91.8 |
| | right ankle | 90.3 |
| 30 minutes | left thigh | 91.2 |
| | left ankle | 86.9 |
| | right thigh | 91.6 |
| | right ankle | 90.3 |
| 35 minutes | left thigh | 91.6 |
| | left ankle | 86.9 |
| | right thigh | 91.8 |
| | right ankle | 90.5 |
| Note - Electrical producing cream was applied to right ankle at 35 minutes. | | |
| 40 minutes | left thigh | 91.4 |
| | left ankle | 86.9 |
| | right thigh | 90.3 |
| | right ankle | 90.5 |
| 45 minutes | left thigh | 91.2 |
| | left ankle | 86.9 |
| | right thigh | 88.7 |
| | right ankle | 90.1 |
| 50 minutes | left thigh | 91.2 |
| | left ankle | 86.4 |
| | right thigh | 89.2 |
| | right ankle | 90.5 |
| 55 minutes | left thigh | 91.2 |
| | left ankle | 87.3 |
| | right thigh | 89.4 |
| | right ankle | 90.1 |

TABLE D-continued

| | | |
|---|---|---|
| Note - At 57 minutes, Patient A reported a cool feeling from above the ankle to the heel. | | |
| 60 minutes | left thigh | 91.4 |
| | left ankle | 87.3 |
| | right thigh | 90.0 |
| | right ankle | 90.1 |
| 65 minutes | left thigh | 91.2 |
| | left ankle | 87.4 |
| | right thigh | 90.5 |
| | right ankle | 90.5 |
| 70 minutes | left thigh | 91.0 |
| | left ankle | 87.3 |
| | right thigh | 90.7 |
| | right ankle | 90.1 |

[A]Five minutes after application to left calf and lower thigh (0 time).

Patient A rose from the table at 78 minutes, and the thigh probes were removed. Patient A held the readout portion of the thermometers in her hand while the probes were still attached to the ankles to allow her to walk to the restroom and take a further readout of her ankles after 5 minutes elapsed. However, at 82 minutes the left ankle probe came loose so no reading was taken. The right ankle probe gave a reading of 81.1° F. at 82 minutes. Patient A reported that her left side (neuropathic side) felt soothed.

Example 3

Treatment of Patient B

1. Patient History

The topical electrical producing cream prepared in Example 1 was used to treat a second patient (hereinafter referred to as "Patient B"). Patient B was a 60-year old, 5'7", Caucasian female. She was a non-insulin dependent diabetic and had sensory neuropathy that was worse in her right leg. She did not have any visible wounds. Her daily oral medications were Glucophage (1 in the evening), Toprol, Diovan, and Lipitor (1 in the evening).

2. Treatment with Inventive electrical Producing Creams

The ambient temperature during treatment ranged from 74-75° F. according to measurements from the four different Stress Thermometers as described in Part 2 of Example 2. The probes were applied as described in Part 2 of Example 2. The initial readings are shown in Table E.

TABLE E

| PROBE LOCATION | TEMPERATURE[A] | TEMPERATURE[C] |
|---|---|---|
| left thigh | 88.7° F. | 89.1° F. |
| left ankle | 83.8° F. | 83.8° F. |
| right thigh | 79.0° F.[B] | 90.7° F. |
| right ankle | 86.5° F. | 86.5° F. |

[A]Temperature prior to electrical producing cream application.
[B]The probe came loose from the right thigh, thus resulting in the 79° F. reading.
[C]Temperature at 4 minutes after temperature reading in middle column.

Temperature readings were taken as described in Part 2 of Example 2. These readings and the times of electrical producing cream application to Patient B's legs are set forth in Table F.

TABLE F

| TIME | LOCATION | TEMPERATURE (° F.) |
|---|---|---|
| 5 minutes[A] | left thigh | 90.5 |
| | left ankle | 81.5 |

TABLE F-continued

| | | |
|---|---|---|
| | right thigh | 91.6 |
| | right ankle | 86.2 |
| Note - The inventive electrical producing cream was applied to the entire left leg at 5 minutes. At 7 minutes, Patient B reported that her left leg was cool. | | |
| 10 minutes | left thigh | 90.5 |
| | left ankle | 81.5 |
| | right thigh | 91.9 |
| | right ankle | 85.8 |
| 15 minutes | left thigh | 90.7 |
| | left ankle | 81.5 |
| | right thigh | 92.3 |
| | right ankle | 85.8 |
| 20 minutes | left thigh | 90.9 |
| | left ankle | 81.1 |
| | right thigh | 92.1 |
| | right ankle | 85.5 |
| Note - Patient B reported feeling a stinging sensation behind her left knee, and that the toes on her left foot felt strange. | | |
| 25 minutes | left thigh | 91.0 |
| | left ankle | 81.1 |
| | right thigh | 92.3 |
| | right ankle | 84.7 |
| Note - Patient B reported that she still felt a stinging sensation behind her left knee. | | |
| 30 minutes | left thigh | 91.6 |
| | left ankle | 81.1 |
| | right thigh | 92.8 |
| | right ankle | 84.7 |
| 35 minutes | left thigh | 91.6 |
| | left ankle | 81.1 |
| | right thigh | 93.0 |
| | right ankle | 82.9 |
| Note - The inventive electrical producing cream was applied to the entire right leg at 35 minutes. | | |
| 40 minutes | left thigh | 91.9 |
| | left ankle | 81.0 |
| | right thigh | 93.6 |
| | right ankle | 83.3 |
| 45 minutes | left thigh | 92.1 |
| | left ankle | 80.6 |
| | right thigh | 93.6 |
| | right ankle | 83.7 |
| Note - Patient B reported feeling a burning on her left side. She stated that her right leg felt cool, and that she felt a sensation as if a thumb were being pressed into the middle of the arch on her right foot. She reported that she had a stress fracture of the calchaneal bone on the right heel. | | |
| 50 minutes | left thigh | 91.9 |
| | left ankle | 80.2 |
| | right thigh | 93.6 |
| | right ankle | 83.7 |
| Note - Patient B reported that she thought the doctor was touching her right foot, but he was not. | | |
| 55 minutes | left thigh | 91.9 |
| | left ankle | 80.1 |
| | right thigh | 93.7 |
| | right ankle | 83.3 |
| Note - Patient B reported that her left leg was feeling restless. | | |
| 60 minutes | left thigh | 92.7 |
| | left ankle | 80.1 |
| | right thigh | 93.9 |
| | right ankle | 83.3 |
| 65 minutes | left thigh | 93.0 |
| | left ankle | 80.1 |
| | right thigh | 94.1 |
| | right ankle | 83.3 |
| Note - Patient B rose at 66 minutes. | | |
| 70 minutes | left thigh | 91.0 |
| | left ankle | 79.7 |
| | right thigh | 91.0 |
| | right ankle | 82.8 |

[A]Five minutes after first temperature reading in Table E.

The probes were removed after 70 minutes.

Example 4

Determination of Metabolic Activity

The topical electrical producing cream prepared in Example 1 was applied to the left inner forearm (below the elbow) of a patient. The treated area was then swabbed with a glass slide that was subsequently sandwiched between two ECG patches attached to leads to a Radio Shack digital, multi-meter. The initial reading (time=0) was 0.0 mV. Subsequent readings were taken at different intervals, and those results are reported in Table G.

TABLE G

| TIME (minutes after initial reading) | READING (mV) |
| --- | --- |
| 1 | 0.2 |
| 32 | 0.9 |
| 33 | 0.8 |
| 43 | 0.9 |
| 51 | 1.0 |
| 52 | 0.9 |
| 56 | 1.0 |
| 72 | 1.2 |
| 73 | 1.4 |
| 74 | 1.2 |
| 121 | 1.5 |

This test was carried out to show that oxygen activation from the compounded electrical producing cream occurs following the application to human skin with or without sweat.

This test was repeated using electrical producing cream that had been swabbed from another patient's back. However, the cream tuned green in color and did not reproduce similar results with the ECG patches. It also took about 6 hours and 20 minutes for this person to notice the heat activation in the location where the electrical producing cream had been applied to the back.

Example 5

Metabolic Activity Comparison

Figure 1B:
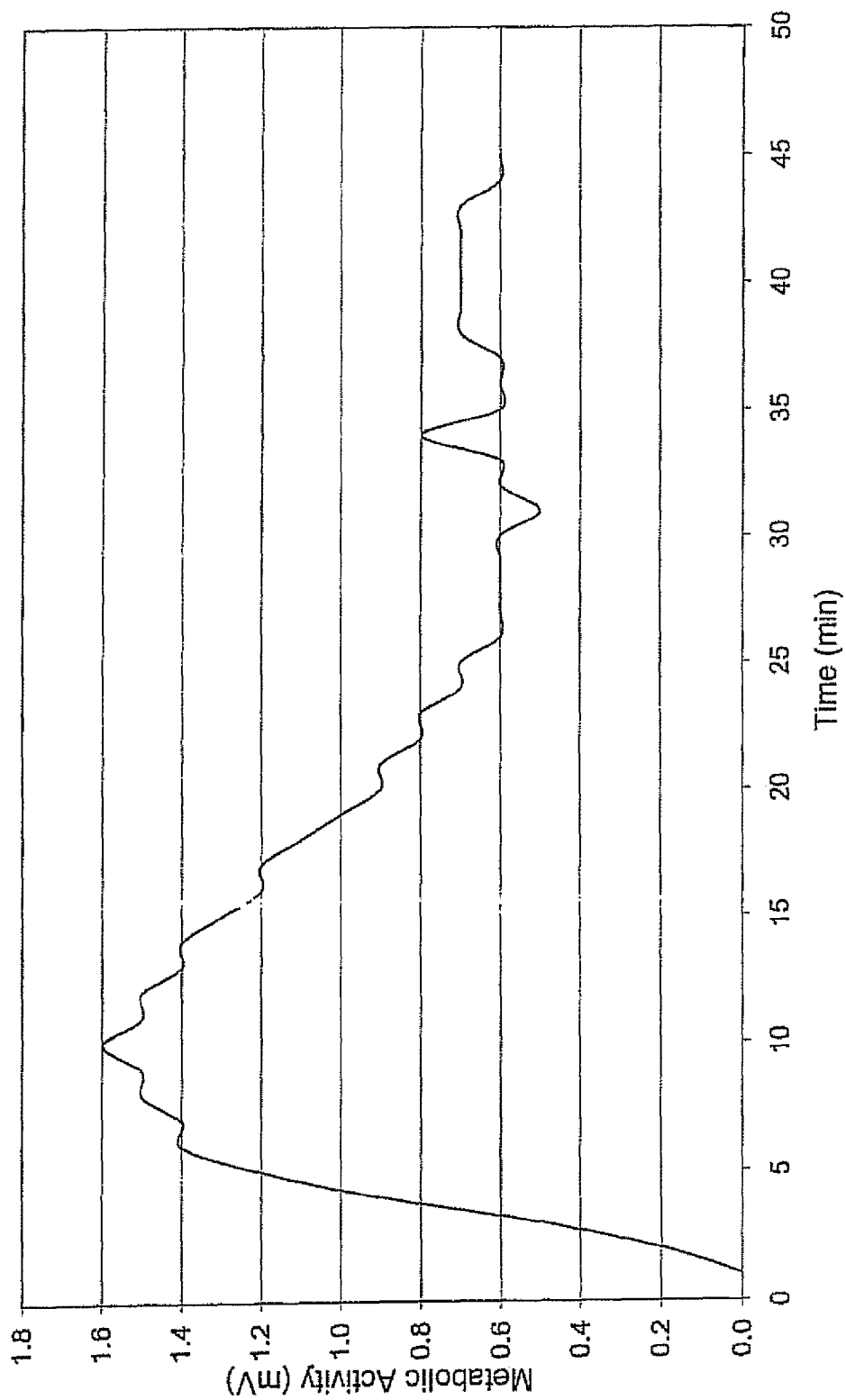
FIG. 1b is a graph depicting the metabolic activity of another prior art product over a 45-minute time period.
Figure 1D:
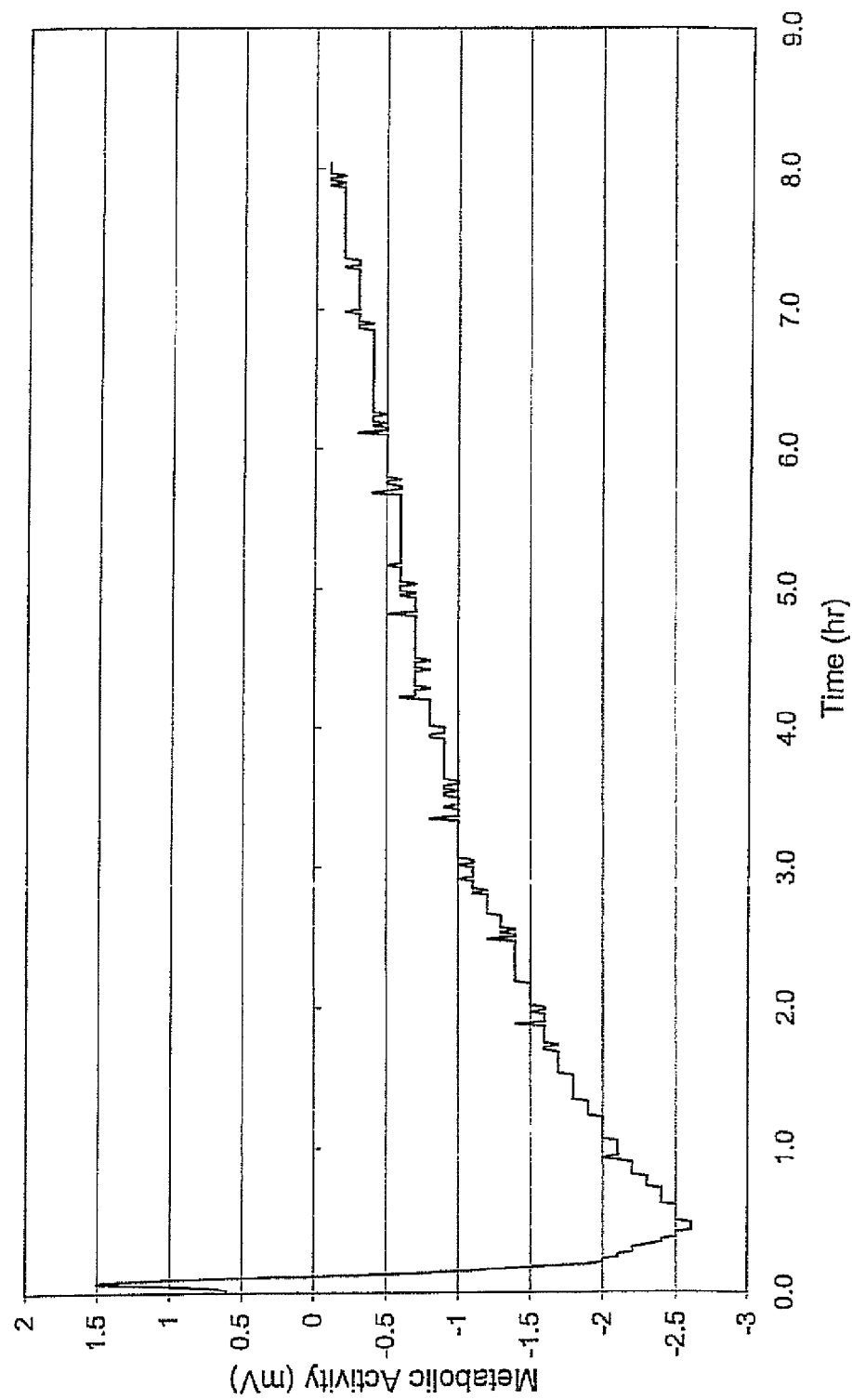
FIG. 1d is a graph depicting the metabolic activity of the inventive electrical producing cream over an 8-hour time period.
Figure 2:
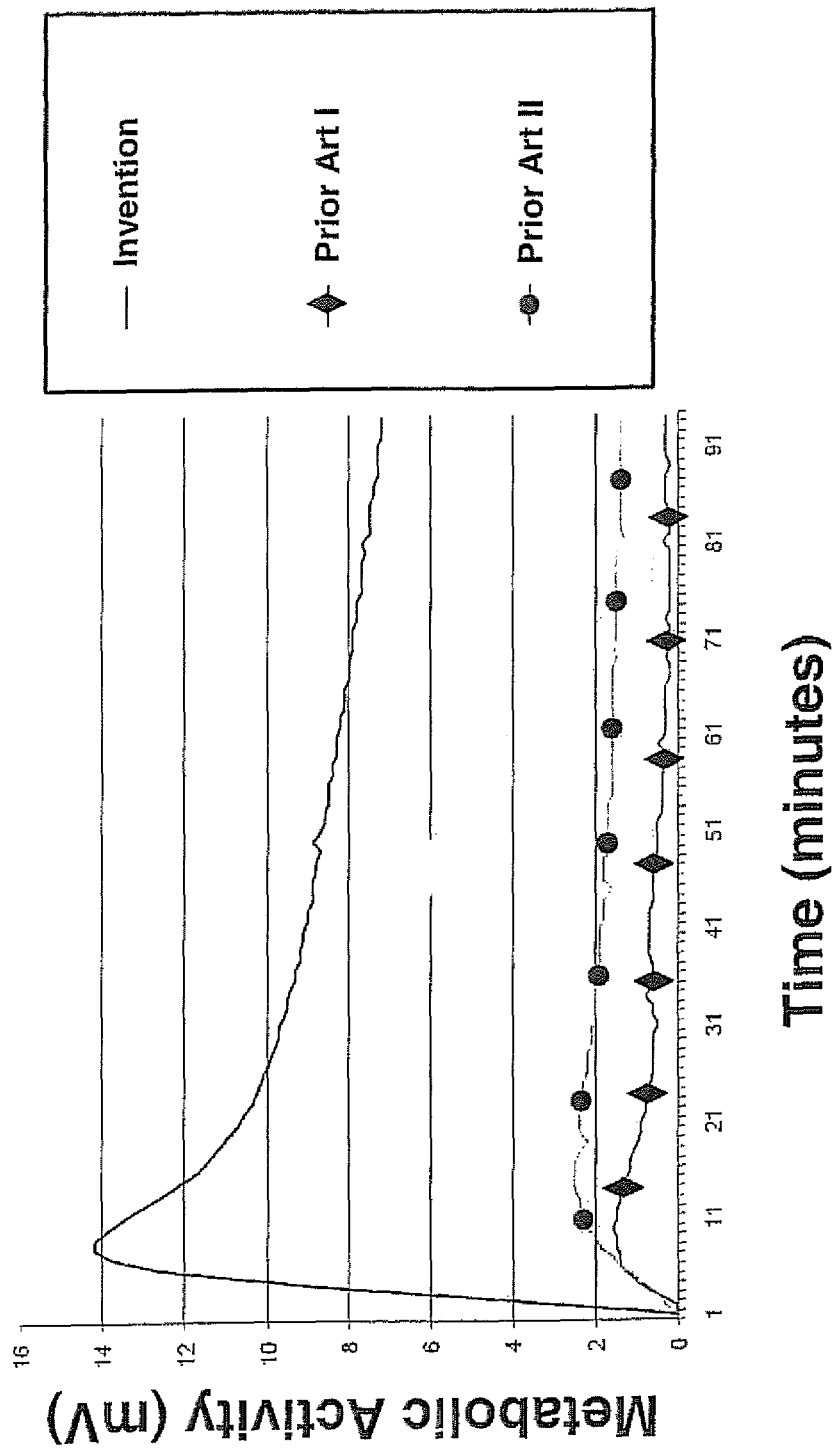
FIG. 2 is a graph depicting the metabolic activity of the inventive electrical producing cream compared to two prior art products.

In this test, the metabolic activity of the topical electrical producing cream prepared in Example 1 was determined following the steps set forth in Example 4. The same steps were followed to determine the metabolic activity of two prior art products. FIG. 1a shows the metabolic activity of one prior art product (non-modified SOMBRA) over a 45-minute time period. FIG. 1b shows the metabolic activity of another prior art product (non-modified BIO-FREEZE) over a 45-minute time period. FIG. 1c shows the inventive electrical producing cream's metabolic activity over a 45-minute time period. A comparison of these figures shows that metabolic activity of the prior art peaks and then drops substantially over the 45-minute time period while the inventive electrical producing cream's metabolic activity maintains very high levels even after peaking. FIG. 1d shows the electrical producing cream's metabolic activity over an 8-hour time period. This graph shows that this activity drops slowly over the 8-hour time period, thus providing prolonged treatment periods as compared to prior art products.

Example 6

Treatment of Patient with Inventive Electrical Producing Creams

The patient in this example (hereinafter referred to as "Patient C") was a Caucasian female in her late 50s. Patient C was suffering from neuropathy in her feet, with symptoms including sharp, stabbing pains and contractures due to over-stimulation of muscles. The condition had caused Patient C to take disability from work.

The topical electrical producing cream prepared in Example 1 was applied to Patient C's feet. Within 10 minutes, the contractures in her feet started to release, and she reported that her feet felt 90% better. Also, the sharp, stabbing pain was relieved for 6 hours after treatment.

Example 7

Preparation of Topical Electrical Producing Cream

Purified water was mixed with Carbopol® Ultrez 20 by stirring in a 1-gallon jug to evenly disperse the polymer. Camphor gum and menthol crystals were then mixed together and then added to the ingredients in the jug.

Next, the following ingredients were mixed together until a homogenous mixture was formed: glycerin, decyl glucoside (Plantaren® 2000 available from Cognis Corporation), capsaicin frutescens oleoresin, boswellin extract, zingiber officinale (ginger) root extract, bromelaine extract, *salix alba* (willow) bark extract, *arnica cordifolia* extract, aloe vera gel, *hamamelis virginiana* (witch hazel), and *camellia sinensis* (green tea) leaf extract. This mixture was then added to the ingredients in the jug and stirred until the mixtures were completely combined.

Then, potassium amino acid chelate was mixed with AEROBIC 07 (sodium chlorite, carbonates, and bicarbonates), and added to the ingredients in the jug. The ingredients in the jug were stirred until the potassium and oxygen sources were completely incorporated.

Next, sodium hydroxymethylglycinate (Suttocide® A available from International Specialty Products) was added to the ingredients in the jug and mixed by stirring. Finally, a small amount of fragrance was added to the ingredients in the jug and mixed by stirring to yield the final electrical producing cream.

The percentages by weight of the total ingredients in the electrical producing cream are set forth in Table H, below.

TABLE H

| INGREDIENTS | % BY WEIGHT[A] |
| --- | --- |
| Purified Water | 83.100 |
| Carbopol Ultrez 20 | 0.850 |
| Camphor Gum | 3.100 |
| Menthol Crystals | 3.000 |
| Glycerin | 4.000 |
| Decyl Glucoside | 1.000 |
| *Capsicum Frutescens* Oleoresin | 0.250 |
| Boswellin Extract | 0.010 |
| Ginger Root Extract | 0.010 |
| Bromelaine Extract | 0.010 |
| Willow Bark Extract | 0.100 |
| *Arnica Cordifolia* Extract | 0.200 |
| *Aloe Vera* Gel | 0.300 |
| Witch Hazel Extract | 3.000 |
| Green Tea Leaf Extract | 0.100 |
| Potassium Amino Acid Chelate | 0.090 |
| Sodium Chlorite | 0.010 |
| Carbonates | 0.010 |
| Bicarbonates | 0.010 |
| Sodium Hydroxymethylglycinate | 0.600 |
| Fragrance | 0.250 |

[A]Percentages are based upon the total weight of all ingredients in the electrical producing cream taken as 100% by weight.

Example 8

Treatment of Patient with Inventive Electrical Producing Cream

The topical electrical producing cream prepared in Example 7 was used to treat a patient (hereinafter referred to as "Patient D"). Patient D was a Caucasian female, 60 years old, and she was 5'1" approximately 160 lbs. Patient D had originally fractured her back in a skiing accident in 1969. In 1988, Patient D underwent two surgeries where surgeons removed segments of a disc that had worn a hole into the patient's spinal chord. More than 10 years later, Lumbar Vertebras L4/L5/S1 were fused together due to instability and movements. In 2005, the patient had a Dynesys® Spine System device implanted to keep the Lumbar Disc open at L2/L3/L4. Subsequently, the patient had a Spinal Chord Implant installed with a control device imbedded into the upper buttocks.

At the time of treatment, the patient exhibited the following conditions: arthritis, spinal stenosis, spinal chord arachnoditis, scar tissue adhesions, right low back nerve damage with radiating symptoms into mainly the right leg into the foot, and was in need of a knee replacement to the left knee. The patient's left knee had severely restricted range of motion due to arthritis and swelling (edema). The patient's left foot was also infected. The patient's posterior/anterior thoracolumbar spinal movement was also extremely limited.

The topical electrical producing cream prepared in Example 7 was applied to the left knee of the patient. After 30 minutes, the patient exhibited a significantly increased range of motion of the left knee, and reported that movement of the knee was less painful.

The topical electrical producing cream prepared in Example 7 was then applied to the patient's back along the thoracolumbar spine area. After 15 minutes, the patient's forward range of motion was significantly increased, and the patient reported that she was able to comfortably bend forward much farther than before the electrical producing cream had been applied. After 30 minutes, the patient was asked to bend forward again, and the patient's range of motion was measured with a JTECH Dualer IQ™ Inclinometer, available from JTECH Medical. The results indicated that the patient's throacolumbar range of motion had increased by 14 degrees, 30 minutes after application of the topical electrical producing cream. Patient D also reported that the implanted Spinal Chord stimulator was not needed for over 24 hours after application of the topical electrical producing cream due to temporary relief of chronic symptoms.

Figure 3A:
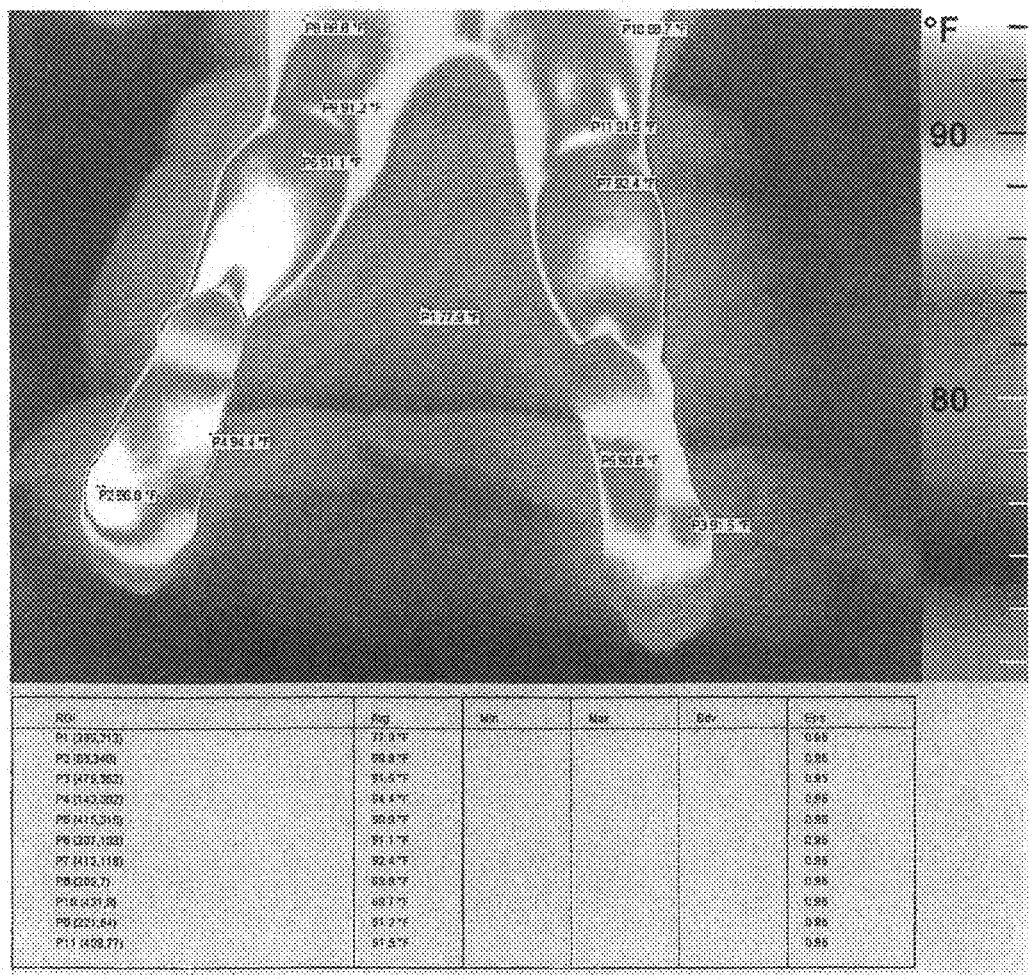
FIG. 3a is a thermal image scan from Example 8, taken of Patient D's lower extremities before beginning treatment with the inventive electrical producing cream.

Patient D was then laid face down on a treatment table and a thermal image scan (FIG. 3a) was taken of the patient's lower extremities and specific data points on the patient's legs and feet were recorded. The patient's left foot temperature was greatly elevated due to the infection. There was also a noticeable difference between the right and left feet, attributed to the spinal chord and nerve root injuries to the right lower back. The topical electrical producing cream prepared in Example 7 was then applied to the top and bottom of each calf, ankle, and foot.

Figure 3B:
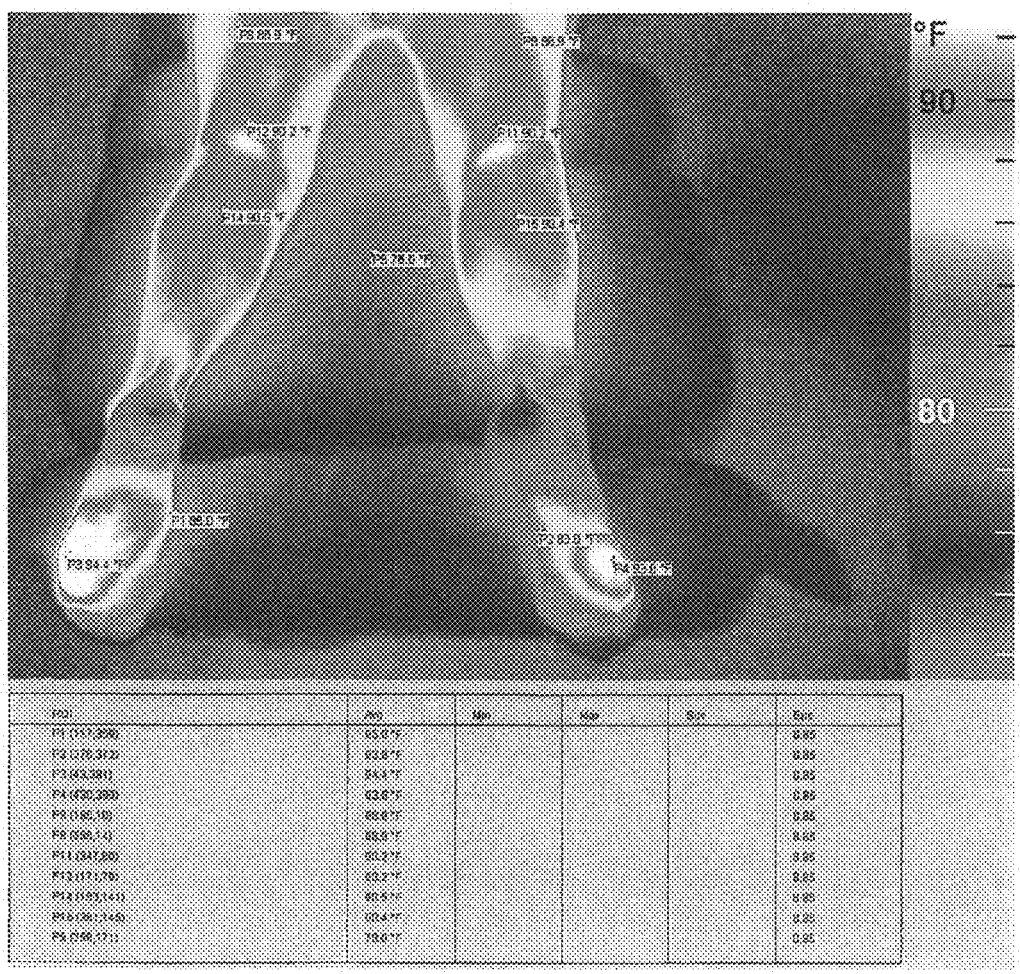
FIG. 3b is a thermal image scan from Example 8, taken of Patient D's lower extremities 30 minutes after treatment with the inventive electrical producing cream.

After 30 minutes another thermal image scan (FIG. 3b) was taken of the patient's lower extremities and the data was recorded. No patient movement was allowed during this time.

The temperature of the left foot was greatly reduced due to increased nerve and circulation function. It was also observed that there was less of a temperature difference between the right and left feet, as the temperature of the left foot decreased and the temperature of the right foot increased.

After 50 minutes another thermal image scan was taken of the patients lower extremities and the final temperature for selected data points were recorded.

The results of the thermal image scans are provided below in Table I. The ambient temperature of the room ranged from 77.9-78° F.,

TABLE I

| DATA POINT | TEMPERATURE (° F.) at RECORDED TIMES | | |
|---|---|---|---|
| | 0 minutes | 30 minutes | 50 minutes |
| ball of left foot | 96.8 | 94.4 | 92.5 |
| arch of left foot | 94.4 | 85.0 | |
| left calf | 91.1 | 90.5 | 88.1 |
| left knee | 91.2 | 90.2 | |
| left thigh | 88.8 | 88.9 | 88.6 |
| ball of right foot | 91.5 | 93.8 | 92.1 |
| arch of right foot | 90.9 | 83.8 | |
| right calf | 92.4 | 90.4 | 88.3 |
| right knee | 91.5 | 90.2 | |
| right thigh | 88.7 | 88.9 | 87.5 |

Before beginning treatment, the average temperature difference between the patient's right and left legs and feet was about 4.3° F., After 50 minutes, the average temperature difference between the patient's right and left legs and feet was decreased to about 0.4° F. The topical electrical producing cream was observed to increases circulation in infected area, lowering the temperature, while simultaneously increasing circulation in the area of nerve damage and raising the temperature.

Example 9

Treatment of Patient with Electrical Producing Cream

The electrical producing cream prepared in Example 7 was used to treat and/or relieve symptoms of Multiple Sclerosis in a patient (hereinafter referred to as "Patient E"). Patient E was a female, 55 years old, 5'11" tall and approximately 180 lbs. In 1997, Patient B was diagnosed with Multiple Sclerosis. Patient E exhibited reduced range of motion in the right knee flexion.

Patient E was laid face down on a treatment table and asked to bend her right knee to bring her heel towards her thigh. The patient was able to flex her knee approximately 5 degrees.

Next, the electrical producing cream was applied to the patient's right leg on and around the knee area. After 20 minutes, the patient was again asked to bend her right knee to bring her heel towards her thigh. Due to the stimulation of the patient's nervous system by the electrical current (mV) produced by the inventive cream, the patient's range of motion in the right knee flexion was visually observed to increase by approximately 20 degrees, for a total flexion of 25 degrees.

Example 10

Treatment of Patient with Electrical Producing Cream

The electrical producing cream prepared in Example 7 was used to treat and/or relieve symptoms of Multiple Sclerosis in a patient (hereinafter referred to as "Patient F"). Patient F was a female, 27 years old, 5'3" tall and approximately 102 lbs. In 2001 Patient F was diagnosed with Multiple Sclerosis, and is now living in an assisted-living environment and unable to care for herself Patient F exhibited multiple physical impairments. For example, all of the patient's movement in the extremities and trunk of her body were rigid/ratcheting tremor movements. The patient was unable to steady her hands to put her glasses on with one hand, such that she used both hands making several attempts to position her glasses correctly. The patient's mobility was restricted to using a walker to get around. Without the walker, the patient would stammer towards an object and fall into it if near enough. Severe tremors were observed while the patient was laying down or attempting to stand with the walker.

Patient F was laid face down, with assistance, on a treatment table and asked to keep her knees straight and raise her right leg into the air. The patient was able to lift her right leg high enough to obtain an angle of 17 degrees. Next she was asked to keep her knee straight and raise her left leg into the air. The patient was able to lift her left leg high enough to obtain an angle of 11 degrees.

Next, the electrical producing cream prepared in Example 7 was applied to the patient's right and left legs and right and left arms and lumbar area. After 15 minutes, the patient was again asked to keep her knees straight and raise her right leg into the air. The patient was able to lift her right leg to an angle of 26 degrees with reduced tremors. Next she was asked to keep her knees straight and raise her left leg into the air. The patient was able to lift her left leg to an angle of 20 degrees with reduced tremors.

Next, Patient F was asked to get up and walk towards a dining area that was about 120 feet away, using her walker. The patient stood up and proceeded to walk towards the door of her room, towards the dining room. After the patient reached her room door with the walker, she took it upon herself to grasp an assistance rail on the wall and leave her walker behind. Patient F continued towards the dining area without assistance, using the rail and periodically grasping it for increased support, but never for more than 15 feet at a time. Patient F sat down at a dining table and was observed to place her glasses on using only her right hand and with little ratcheting tremors. Next she was observed for 15 minutes from a distance while eating. Due to the stimulation of the patient's nervous system by the electrical current (mV) produced by the inventive cream, Patient F was able to bring food to her mouth with little trouble, and it was observed that the ratcheting tremors were greatly reduced. The patient reported that the effects of the electrical producing cream lasted for several hours, allowing for an increased quality of life while performing what are called "simple daily activities."

All recorded angle measurements were determined using a JTECH Dualer IQ™, Inclinometer, available from JTECH Medical, placing the Inclinometer on the back of the thighs for measurements.

I claim:

1. An electrical producing cream comprising from about 0.005%-15% by weight potassium, and a source of oxygen sufficient to provide at least about 0.005% by weight oxygen, said percentages based upon the total weight of the electrical producing cream taken as 100% by weight, said cream having a peak metabolic activity of at least about 30 mV.

2. The electrical producing cream of claim 1, wherein said source of oxygen is selected from the group consisting of chlorites, spirulina, and mixtures of the foregoing.

3. The electrical producing cream of claim 2, wherein said source of oxygen is an alkali metal chlorite.

4. The electrical producing cream of claim 1, said electrical producing cream further comprising at least one active ingredient selected from the group consisting of camphor, menthol and capsicum.

5. The electrical producing cream of claim 4, said electrical producing cream comprising from about 0.005-22% by weight camphor.

6. The electrical producing cream of claim 4, said electrical producing cream comprising from about 0.005-20% by weight menthol.

7. The electrical producing cream of claim 1, said electrical producing cream further comprising at least one additional ingredient selected from the group consisting of aloe vera, arnica, bosweila, bromelaine, capsicum, carbonates, bicarbonates, decyl glucoside, distilled water, deionized water, ginger, glycerine, green tea extract, sodium hydroxymethyl glycinate, willow bark, witch hazel, fragrance, thickener, and mixtures of the foregoing.

8. The electrical producing cream of claim 7, said electrical producing cream comprising from 0.001-8% by weight capsicum.

9. The electrical producing cream of claim 1, wherein said electrical producing cream is provided in a form selected from the group consisting of lotion, cream, gel, spray, and solid.

10. An electrical producing cream comprising:
an active ingredient selected from the group consisting of analgesics, anesthetics, antipruritics, antihistamines, and counterirritants;
potassium; and
a source of oxygen, said electrical producing cream having a peak metabolic activity of at least about 30 mV.

11. The electrical producing cream of claim 10, said analgesics, anesthetics, antipruritics, antihistamines, and counterirritants being selected from the group consisting of menthol, camphor, and capsicum.

* * * * *